United States Patent [19]

Marquis et al.

[11] Patent Number: 4,758,681

[45] Date of Patent: Jul. 19, 1988

[54] METHOD OF MAKING MOLYBDENUM/ALKYLENE GLYCOL COMPLEXES USEFUL AS EPOXIDATION CATALYSTS

[75] Inventors: Edward T. Marquis; Howard F. Payton, both of Austin, Tex.

[73] Assignee: Texaco Chemical Company, White Plains, N.Y.

[21] Appl. No.: 947,672

[22] Filed: Dec. 30, 1986

[51] Int. Cl.$^4$ .............................................. C07F 11/00
[52] U.S. Cl. ..................................................... 556/57
[58] Field of Search .......................................... 556/57

[56] References Cited

U.S. PATENT DOCUMENTS

| | | | |
|---|---|---|---|
| 3,285,942 | 11/1966 | Price et al. | 536/57 |
| 3,991,090 | 11/1976 | Hagstrom et al. | 556/57 |
| 4,009,122 | 2/1977 | Lines et al. | 556/57 X |
| 4,607,113 | 8/1986 | Shum et al. | 556/57 |
| 4,626,596 | 12/1986 | Marquis et al. | 556/57 |
| 4,650,886 | 3/1987 | Marquis et al. | 556/57 |
| 4,654,427 | 3/1987 | Marquis et al. | 556/57 |
| 4,667,045 | 5/1987 | Briggs et al. | 556/57 X |

Primary Examiner—Paul F. Shaver
Attorney, Agent, or Firm—Jack H. Park; Kenneth R. Priem; Carl G. Ries

[57] ABSTRACT

An improved procedure for making molybdenum/ethylene glycol complexes useful as epoxidation catalysts wherein the cycle time necessary for catalyst preparation is significantly reduced by preparing a mixture of undiluted ethylene glycol with undiluted ammonium dimolybdate in the molar ratio of about 7 to about 20 moles of ethylene glycol per gram atom of molybdenum, heating the mixture from ambient conditions to a temperature of about 25° to about 150° C. over a 5 to 100 minute period while simultaneously reducing the pressure to about 5 to about 100 mm Hg and, after an appropriate holding time, if necessary, returning the mixture to ambient conditions and recovering an essentially solids free clear catalytically active solution of molybdenum/ethylene glycol complex in unreacted ethylene glycol having a molybdenum content of about 10 to 15 wt. % of molybednum.

5 Claims, No Drawings

METHOD OF MAKING MOLYBDENUM/ALKYLENE GLYCOL COMPLEXES USEFUL AS EPOXIDATION CATALYSTS

BACKGROUND OF THE INVENTION

1. Field of the Invention

The invention relates to a method for making molybdenum compounds and more particularly relates to an improved method for making molybdenum alcohol complexes useful as olefin epoxidation catalysts.

2. Other Related Methods in the Field

The epoxidation of olefins to give various epoxide compounds has long been studied by those skilled in the art. It is well known that the reactivities of the various olefins differs with the number of substituents on the carbon atoms involved in the double bond. Ethylene itself has the lowest relative rate of epoxidation, with propylene and other alpha olefins being the next slowest. Compounds of the formula $R_2C=CR_2$, where R simply represents alkyl or other substituents, may be epoxidized fastest. Thus, the more substituents on the double bond carbons, the easier it is to epoxidize across that bond.

The production of ethylene oxide from ethylene has long been accomplished by reaction with molecular oxygen over a silver catalyst. Numerous patents have issued on various silver-catalyzed processes for the production of ethylene oxide. Unfortunately, the silver catalyst route has not been commercialized for olefins other than ethylene. For a long time the commercial production of propylene oxide could only be accomplished via the cumbersome chlorohydrin process.

Another commercial process for the manufacture of substituted oxides from alpha olefins such as propylene was not discovered until John Kollar's work in the 1960s. His U.S. Pat. No. 3,351,635 taught that an organic oxide compound could be made by reacting an olefinically unsaturated compound with an organic hydroperoxide in the presence of a molybdenum, tungsten, titanium, columbium, tantalum, rhenium, selenium, chromium, zirconium, tellurium or uranium catalyst. Kollar's U.S. Pat. No. 3,350,422 teaches a similar process using a soluble vanadium catalyst.

However, even though Kollar's work was recognized as extremely important in the development of a commercial propylene oxide process that did not depend on the chlorohydrin route, it has been recognized that Kollar's catalytic route (in which molybdenum is the preferred catalyst) has a number of problems. For example, large quantities of the alcohol corresponding to the peroxide used were formed. When t-butyl hydroperoxide is used as a co-reactant, essentially equimolar amounts of the olefin epoxide and t-butyl alcohol are formed. Other troublesome by-products were the olefin oligomers. If propylene is the olefin to be epoxidized, various propylene dimers, sometimes called hexenes, are usually formed. Besides being undesirable in that this is not the desired use of propylene, problems are caused in separating the desired propylene oxide from the product mix. In addition, the molybdenum catalyst may not be stable or the recovery of the catalyst for recycle may be poor.

Various avenues of investigation have been explored in attempts to improve on the molybdenum-catalyzed epoxidation of propylene. One technique was to try to improve on the catalyst itself. Patents which cover the preparation of various molybdenum epoxidation catalysts include U.S. Pat. No. 3,362,972 to Kollar. There a hydrocarbon soluble salt of molybdenum or vanadium may be made by heating a molybdenum compound in which molybdenum has a valence of +6, or a vanadium compound in which vanadium has a valence of +5, with a carboxylic acid of from 4 to 50 carbon atoms having at least 4 carbon atoms per carboxylic group. U.S. Pat. No. 3,578,690 to Becker discloses that molybdenum acid salts may be made by directly reacting a carboxylic acid with a molybdenum compound while removing the water that is formed.

The reaction of molybdenum trioxide with monohydric saturated alcohols having 4 to 22 carbon atoms or with a mono- or polyalkylene glycol monoalkyl ether or mixtures thereof to make olefin epoxidation catalysts is described in U.S. Pat. No. 3,480,563 to Bonetti, et al. These catalysts have only 0.07 to 0.93% molybdenum, which is a molybdenum content undesirably too low for commercial use. Bonetti, et al. do not realize the importance of the ratio of alcohol to molybdenum compound reactants with respect to maximizing molybdenum content yet providing a soluble, active epoxidation catalyst. They also do not indicate any benefit from adding ammonium hydroxide to the preparation, an important factor discovered when molybdenum trioxide is reacted with 2-ethyl-1-hexanol.

In U.S. Pat. No. 4,434,975 to ARCO, investigators found that molybdenum catalysts could be made from saturated alcohols or glycols having one to four carbon atoms, such as ethylene glycol and propylene glycol, by reacting them with molybdenum metal and an organic hydroperoxide, peroxide, or $H_2O_2$. Molybdenum compounds prepared by reacting an ammonium-containing molybdate with a hydroxy compound, for example, an organic primary or secondary alcohol, a glycol or a phenol, are described in U.S. Pat. Nos. 3,784,482 and 3,787,329 to Cavitt.

Further, U.S. Pat. No. 3,573,226 to Sorgenti discloses that molybdenum-containing epoxidation catalyst solutions may be made by heating molybdenum powder with a stream containing unreacted tertiary butyl hydroperoxide and polyhydric compounds of from about 200 to 300 molecular weight and having from 4 to 6 hydroxyl groups per molecule. These catalysts are used for the epoxidation of propylene according to U.S. Pat. No. 3,666,777 to Sorgenti.

U.S. Pat. No. 3,953,362 to Lines, et al. reveals that novel molybdenum epoxidation catalysts may be prepared by reacting an oxygen-containing molybdenum compound with hydrogen peroxide and an amine and optionally water or an alkylene glycol at elevated temperatures. Similar catalysts are prepared by reacting an oxygen-containing molybdenum compound with an amine and an alkylene glycol at elevated temperatures according to U.S. Pat. No. 4,009,122 also to Lines, et al.

U.S. Patent to Mattucci, et al. also concerns molybdenum glycol catalysts prepared from molybdenum acetyl acetonate and isolated as solids. When the materials are used as epoxidation catalysts, they must be employed in solution with a hydrocarbon solvent. Molybdenum derivative compounds also useful as epoxidation catalysts may be prepared by reacting an oxygen-containing molybdenum compound such as molybdenum acetylacetonate, molybdic acids and molybdenum oxides with an organic compound having vicinal hydroxyl groups in the presence of a hydrohalic acid such as hydrofluoric acid, hydrochloric acid and the like, according to U.S. Pat. No. 3,991,090 to Hagstrom, et al.

Marquis, et al. U.S. Pat. No. 4,626,596, dated Dec. 2, 1986, and entitled "Synthesis of Molybdenum/Alkylene Glycol Complexes Useful as Epoxidation Catalysts" discloses a method of making catalytically active molybdenum complexes wherein a reaction mixture consisting essentially of an undiluted alkylene glycol, such as propylene glycol and an undiluted ammonia-containing molybdenum compound such as ammonium heptamolybdate tetrahydrate mixed in the ratio of 7 to 20 moles of alkylene glycol per gram atom of molybdenum is heated at 80° to 130° C., in the presence of a minor amount of water followed by a mild stripping of the reaction product to provide a molybdenum complex having a final water content of about 0.5 to 6 wt.%.

Copending allowed Marquis, et al. U.S. patent application Ser. No. 06/804,132, filed Dec. 6, 1985, and entitled "Synthesis of Molybdenum Oxide/Alkanol Complexes" now U.S. Pat. No. 4,654,427 discloses a process wherein a $C_6$-$C_{13}$ alkanol such as 2-ethyl-1-hexanol is reacted with a molybdenum oxide, such as molybdenum trioxide by a process which is initiated in the presence of aqueous ammonium hydroxide and conducted at 120° to 190° C. for 3 to 8 hours to substantially completely remove evolved ammonia and water to provide a liquid reaction product of the molybdenum/alkanol complex dissolved in unreacted alkanol.

Marquis, et al. allowed U.S. patent application Ser. No. 06/804,131, filed Dec. 6, 1985, and entitled "Synthesis of Ammonium Molybdate/Alkanol Complexes" now U.S. Pat. No. 4,650,886 is directed to a process wherein a controlled amount of a $C_6$ to $C_{13}$ alkanol, such as 2-ethyl-1-hexanol is reacted with an ammonium molybdate such as ammonium heptamolybdate tetrahydrate in the presence of water at atmospheric pressure at a temperature of 120° to 190° C. for 3 to 8 hours to substantially completely remove evolved ammonia and water to provide a liquid reaction product containing less than 0.1 wt. % of water and composed of the molybdenum/alkanol complex dissolved in unreacted alkanol.

There still exists a need for an epoxidation catalyst that is stable, easy to prepare, and has a high molybdenum content.

SUMMARY OF THE INVENTION

This invention is directed to an improved method of making molybdenum complexes by reacting an ammonium-containing molybdenum compound with an alkylene glycol at subatmospheric pressure at a temperature ranging from about ambient (e.g., 25° C.) to not more than about 150° C.

DETAILED BACKGROUND DESCRIPTION

Marquis, et al. U.S. Pat. No. 4,626,956 discloses an improved method for making molybdenum/alkylene glycol complexes based, in part, on the discovery that the ratio of alkylene glycol reactant to molybdenum compound has an effect on the ease of filterability of the finished reaction mixture and the stability of the finished complex solution with respect to staying clear and solids-free over extended periods of time. It was also discovered that the actual molybdenum complex preparation history is very important in determing if the final complex is good or poor in its final application as an epoxidation catalyst. It was further discovered in the case of molybdenum complexes made from EG (ethylene glycol) or PG (propylene glycol) used as epoxidation catalysts, that the reaction temperature should not be too high (165° to 180° C.) as this results in low molybdenum contents in the complexes and the formation of large quantities of solids. Also, for complexes useful as epoxidation catalysts, the high molybdenum content must be achieved by adjusting the ratio of glycol to gram atoms of molybdenum, not by distilling off the glycol. If glycol is distilled off to concentrate the molybdenum content of the complex, the water content of the complex will become too low and the complex will perform poorly as an epoxidation catalyst in that the selectivity based on the organic hydroperoxide consumed will be poor. The preferred procedure of U.S. Pat. No. 4,626,956 involves establishing the ratio of moles of glycol to gram atoms molybdenum in the 8:1 to 16:1 range which produces an essentially solids-free reaction mixture after digestion one hour at 90° to 120° C. Next, vacuum stripping is conducted to remove water, ammonia, etc., so that the remaining bottoms are 80 to 95 wt. % of the charge.

DETAILED DESCRIPTION OF THE PREFERRED EMBODIMENT

It has been discovered in accordance with the present invention that molybdenum/ethylene glycol complexes substantially identical to the molybdenum/ethylene glycol complexes of Marquis, et al. U.S. Pat. No. 4,626,596 can be prepared rapidly and effectively by a streamlined subatmospheric preparation process including the steps of mixing ammonium dimolybdate with an excess of ethylene glycol in a reaction vessel under ambient conditions of temperature and pressure, then heating the mixture from ambient temperature (e.g., 25° C.) to about 150° C. with agitation over a period of time ranging from about 5 to about 60 minutes while simultaneously reducing the pressure in the reaction vessel to about 5 to about 150 mm of Hg while removing evolved reaction byproducts as they are formed, next restoring the reaction mixture to ambient conditions of temperature and pressure and recovering the resultant essentially clear reaction product, the reaction product constituting a solution of the molybdenum/ethylene glycol complex in unreacted ethylene glycol having a dissolved molybdenum content of about 10 to about 15 wt. % of molybdenum and containing about 0.5 to about 5 wt. % of water. Preferably, the mixture is heated at 25°–120° C. at a pressure of about 10 to about 80 mm of Mg for about 10 to 50 minutes and held at that temperature for about 4 to 25 minutes. Still more preferably, the mixture is heated at 25°–100° C. and a pressure of about 15–60 mm of Mg for 15 to 40 minutes and held at that temperature for about 6 to 20 minutes.

The molybdenum starting material for the present invention is ammonium dimolybdate.

Ethylene glycol is the other co-reactant used to make the molybdenum complexes of this invention.

The ratio of glycol (moles of ethylene glycol) to gram atoms of molybdenum in the ammonium dimolybdate is important in determining the amount of molybdenum that will be present in the final complex and the ease of processing.

For the ethylene glycol/ammonium dimolybdate system of the present invention, the preferred reactant ratios are 7:1 to 20:1 expressed in terms of moles of ethylene glycol to gram atoms of molybdenum in the ammonium dimolybdate compound. An especially preferred range of moles of glycol to gram atoms of molybdenum is 9:1 to 11:1. To provide the best complex in terms of molybdenum content, ease of processing and stability upon standing, the proportion of water remaining in the complex should be in the range of 0.5 to 5 wt. %. The reaction temperature to make the inventive complexes should be between about 25° to 150° C., preferably 25° to 120° C., and the final pressure must be a subatmospheric pressure of about 5 to about 100 mm of Hg, and more preferably about 10 to about 80 mm of Hg.

The pressure on the reaction mixture should be reduced simultaneously with the heating of the reaction mixture to the desired final temperature, and this step should be performed over a period of about 5 to about 60 minutes, and more preferably about 10 to about 50 minutes. The holding time for the reaction mixture at the final temperature need not be prolonged, and holding times of 7 to 13 minutes have been found to be adequate (see Examples 1, 2 and 3). Generally, no filtration is required for the best complex of this invention. Sufficient overhead is removed during the reaction so that the complex bottoms amount to about 85 to 95 wt. % of the charge and the water content of the catalyst is preferably in the 0.5 to 5.0 wt. % range. Generally, the water content of the final complex should be between about 1 and 3 wt. %, particularly for epoxidation purposes.

The reaction mixture that is formed by the above described process is a clear, essentially solids-free solution of a molybdenum/ethylene glycol complex in unreacted ethylene glycol and may be recovered and used without filtration. The solutions are storage-stable, catalytically active materials having a dissolved molybdenum content of about 10 to about 15 wt. % and a water content of about 0.5 to about 5.0 wt. %. When prepared by the preferred operating procedure, the solutions will normally contain about 11 to 14 wt. % of molybdenum, about 1 to 3 wt. % of water and will constitute about 90–92 wt. % or more of the combined weight of the charge materials.

Since the molybdenum/ethylene glycol complexes of this invention titrate as acids, even though they have no free additional acidic groups, such as carboxylic acid groups, their use as acid catalyst substitutes seems likely. For example, the instant complexes may be useful cyclization catalysts for splitting out water such as in the production of tetrahydrofuran from 1,4-butane diol and the manufacture of triethylenediamine from hydroxyethylpiperazine. The complexes of this invention might be used as catalysts for hydroxylations such as the production of resorcinol from toluene in the presence of a hydroperoxide, carbonate formations from olefins, carbon dioxide and a hydroperoxide, and oxygenate formations from hydrocarbons and organic hydroperoxides. Other catalytic uses for these complexes include condensations, dehydrations, esterifications, oligomerizations, polymerizations, disproportionations and rearrangements other than those mentioned. The molybdenum/glycol complexes could also be tried as corrosion inhibitors in antifreeze formulations and as direct additives to oils, greases and other lubricating fluids.

The molybdenum/ethylene glycol solutions of the present invention are most suitably used as epoxidation catalysts. Before addition to the epoxidation reaction mixture, the complex-catalyst solution is usually premixed with one of the reactants, typically the hydroperoxide, such as a t-butyl alcohol (TBA) solution of t-butyl hydroperoxide (TBHP).

It is well known that soluble molybdenum complexes efficiently catalyze the epoxidation of propylene to propylene oxide in the presence of t-butyl hydroperoxide. The alkylene glycol/molybdenum complexes of this invention surprisingly give selectivities to propylene oxide in such reactions on the order of 98 to 99% and higher at TBHP conversions of about 98 to 98.4% while providing minimal propylene dimer production and very low methyl formate production.

The epoxidations are typically conducted by reacting an olefin with an organic hydroperoxide in the presence of the catalyst and a solvent. Preferably, the olefin is propylene and the hydroperoxide is TBHP. With these reactants, the desired products are propylene oxide (PO) and t-butyl alcohol.

Preferably, the catalyst concentration is from 200 to 600 ppm based on the combination of the olefin and the organic hydroperoxide. Further, the reaction should be conducted at a temperature in the range of 50° to 180° C., preferably 90° to 140° C. and especially in the range of about 100° to 130° C. This reaction temperature is relatively low as compared with other commercial techniques. Another unusual aspect is that the preferred mole ratio of olefin to hydroperoxide is unusually low; on the order of from about 0.9:1 to 3.0:1.

Another preferred embodiment of the epoxidations involves conducting the reaction in two stages, approximately equal in length, with the first stage at a lower temperature than the second stage. For instance, the first hour of reaction would preferably be conducted at a temperature in the range of 50° to 120° C. followed by the second and last hour of reaction at about 120° to 150° C.

The invention will be further illustrated by the following examples, which are given by way of illustration and not as limitations on the scope of this invention.

SPECIFIC EXAMPLES

EXAMPLE 1

9/1 Ratio Moles EG/g Atoms Moly, 20 Minutes Total Preparation Time (6032-25)

To a 500-ml round bottomed flask equipped with magnetic stirrer, thermometer, K-head and condenser was added 191.6 g EG (3.0903 moles) and 58.4 g ammonium dimolybdate (ADM, 0.3435 g atoms moly). Mole ratio of EG/g atoms moly was 9/1. The stirrer was started and a vacuum pulled simultaneously with starting heating. Heating began at 9:15 (25° C.) and at a 30 mm. vacuum. At 9:27 (12 minutes later) the temperature had reached 100° C. (40 mm vacuum). The reaction mixture was light yellow in color with a few solids. Heating at 100° C. continued for only 8 minutes more (40 mm→25 mm) till the reaction mass cleared up—no solids. Heat turned off. Reaction mixture was clear upon cooling—no solids. The entire catalyst preparation took only 20 minutes from heat-up till end of reaction. The overhead in the receiver flask weighed 16.5 g (35.5% water) and the cold trap weighed 1.4 g (87.5% water). The product weight was 227.2 g (90.88% of charge). The product contained 14.0% molybdenum by AA, 2.27% water (KarlFischer), 1.10% $N_2$ by Kjeldahl, and had an acid number of 168.17 mg KOH/gram sample.

EXAMPLE 2

10/1 Ratio Moles EG/g Atoms Moly, 23 Total Minutes Preparation Time (6032-24)

To a flask equipped as above in Example 1 was added 196.2 g EG (3.16452 moles) and 53.8 g ADM (0.3165 g atoms moly). Mole ratio of EG/g atoms moly was 10.0/1. The stirrer started and heating and vacuum began simultaneously. Heating began at 7:55 a.m. and the temperature was 23° C. and the reaction mixture reched 100° C. in only 10 minutes (40 mm). The reaction mixture was light yellow with some solids. Heating was continued at 100° C. for another 13 minutes during which time the vacuum improved from 40 mm to 25 mm and the reaction mixture cleared up—no solids. The entire catalyst preparation took only 23 minutes from the initial heat up to cool down. The overhead weighed 15.7 g (37.9% water). The cold trap weighed 1.6 g (89.83% water). The product weighed 228.1 lg (91.24% of charge). The product contained 13.2% moly and 1.06% water, and 1.16% $N_2$, and had an acid number of 159.24 mg KOH/g of sample.

EXAMPLE 3

11/1 Ratio Moles EG/g Atoms Moly, 20 Total Minutes Preparation Time (6032-26)

To a flask equipped as above in Example 1 was added 200.1 lg EG (3.2274 moles) and 49.9 g of ADM (0.2935 g atoms moly). The mole ratio of EG/g atoms moly was 11.0/1. The stirrer was started and heating and vacuum began at 10:40 a.m. (24° C.). At 10:53 a.m. the reaction mixture reached 100° C. (35 mm)—13 minutes had elapsed since heating started. The reaction mixture was held at 100° C. for an additional seven minutes at 100° C. with the vacuum improving from 35 mm to 30 mm. At this point the reaction mixture was cooled and found free of solids. The entire heat up and reaction time consumed 20 minutes. The overhead weighed 14.9 g (37.68% water). The cold trap weighed 1.2 g (87.47% water). The product weight was 229.7 g. The product contained 11.8% molybdenum (by AA analysis), 2.81% water, 1.09% $N_2$ and had an acid number of 140.65 mg KOH/g sample.

EXAMPLE 4

9/1 Ratio Moles EG/g Atoms Moly; Solids Still Present; 175 Minutes Total Preparation Time (5990-31)

To a 500 ml round bottomed flask equipped with mechanical stirrer, thermometer, $N_2$ inlet, K-head, condenser and receiver flask was added 191.6 g EG (3.0903 moles) and 58.4 g ammonium dimolybdate (ADM, 0.3435 g atoms moly). The mole ratio of EG/g atoms moly was 9/1. The reactants were added to the flask and heat turned on at 8:00 a.m. Atmospheric pressure, nitrogen padded. The reaction mixture reached 100° C. at 8:20 a.m. and was milky in color (20 minutes elapsed). The reaction mixture was held at 100° C. for 1.0 hour (till 9:20 a.m., solids still present) and cooled to 60° C. (10:35 a.m.) at which time a vacuum was pulled (35 mm) and reheating to 100° C. begun—at 10:47 a.m. (45 mm) the reaction temperature reached 100° C. and the reaction mixture held at 100° C. under vacuum (45 mm) for an additional 8 minutes (till 10:55 a.m.). The catalyst preparation was cooled at this point and found to be clear—no solids. From initial heat up to cool down the preparation required 2 hours and 55 minutes (175 minutes). The overhead weighed 9.5 g (49.85% water). The cold trap weighed 1.0 g (92.42% water) and the product weighed 234.7 g (93.88% of the charge). The product was analyzed and found to contain 13.5% molybdenum, 1.21% $N_2$, 2.32% water, and have an acid number of 164.91 mg KOH/g sample.

EXAMPLE 5

10/1 Ratio Moles EG/g Atoms Moly, 100 Minutes Total Preparation Time (5990-38)

To a flask equipped as above in Example 4 was added 196.2 g EG (3.164 moles) and 53.80 g ADM (0.3165 g atoms moly). The mole ratio of EG/g atoms moly was 10/1. The reactants were added to the flask at 10:55 a.m. and the heat turned on (atmospheric pressure, $N_2$ pad). The reaction mixture reached 100° C. at 11:10 a.m. (15 minutes) and heating at 100° C. was continued for 1.0 hour until 12:10 p.m. and then cooled rapidly to 85° C. in five minutes (total time elapsed 1 hour, 20 minutes). The reaction mixture was reheated to 100° C. under vacuum (45 mm initially) and reached 100° C. in only 10 minutes (30 mm), it was further held at 100° C. for 10 minutes under vacuum (30 mm) and then cooled. It was solids free. The final cooling began at 12:35 p.m. From initial heat up to cool down, this preparation required 1 hour and 40 minutes (100 minutes). The overhead weighed 13.6 g (49.39% water) and the cold trap weighed 1.9 g (92.96% water). The product weighed 229.9 g (91.96% of charge). The product was analyzed and found to contain 13.2% molybdenum, 1.07% nitrogen, 1.54% water and have an acid number of 156.81 mg KOH/g sample.

EXAMPLE 6

11/1 Ratio Moles EG/g Atoms Moly, 118 Minutes Total Preparation Time (5990-47)

To a flask equipped as above in Example 4 was added 200.12 g EG (3.228 moles) and 49.88 g ADM (0.3074 g atoms moly). The mole ratio EG/g atoms moly was 11.0/1. The reactants were added to the flask at 7:35 a.m. and heating began (23° C., $N_2$ pad, atmospheric pressure). At 7:55 a.m. (20 minutes) the reaction mixture reached 100° C. and was held there at 100° C. for 1.0 hour (8:55 a.m.) before cooling rapidly to 65° C. (required 15 minutes—now 9:10 a.m.) At 65° C. the vacuum was established (35 mm) and heating began (9:10 a.m.)—the reaction mixture reached 100° C. some 13 minutes later (9:23 a.m.) and the vacuum was improved to 25 mm. The reaction mixture was held an additional 10 minutes at 100° C. (25 mm vacuum) and examined (9:33 a.m.) and found solids free and final cooled. Total preparation time from initial heat up to cool down was 1 hour and 58 minutes (118 minutes). The overhead weighed 14.3 g (40.50% water) and the cold trap weighed 1.9 g (91.93% water). The product weighed 229.2 g (91.68% of charge) and was analyzed and found to contain 11.9% molybdenum (by AA, theory=12.29%), 0.92% nitrogen, 1.24% water, and have an acid number of 143.44 mg KOH/g sample.

TABLE I

Laboratory Catalyst Preparation - Preparation Procedure Study - Catalysts Made from Ammonium Dimolybdate and Ethylene Glycol
Ammonium Dimolybdate (Climax) $(NH_4)_2MO_2O_7$ % Moly = 56.47%

| Example NB Run # | ROH | G.ROH | M.ROH | G.ADM | GA.MO | MR.A/M | Rxn Temp °C. | Rxt Hrs |
|---|---|---|---|---|---|---|---|---|
| 1 6032-25 | EG | 191.52 | 3.081 | 58.38 | .3435 | 9.00 | — | — |
| | | (No Digestion Step - Heat/Pull Vac Simultaneously) | | | | | | |
| 4 5990-31 | EG | 191.52 | 3.081 | 58.38 | .3435 | 9.00 | 100 | 1.0 |
| 2 6032-24 | EG | 196.20 | 3.164 | 53.80 | .3165 | 10.00 | — | — |
| | | (No Digestion Step - Heat/Pull Vac Simultaneously) | | | | | | |
| 5 5990-38 | EG | 196.20 | 3.164 | 53.80 | .3165 | 10.00 | 100 | 1.0 |
| 3 6032-26 | EG | 200.12 | 3.228 | 49.88 | .2934 | 11.00 | — | — |
| | | (No Digestion Step - Heat/Pull Vac Simultaneously) | | | | | | |
| 6 5990-47 | EG | 200.12 | 3.228 | 49.88 | .2934 | 11.00 | 100 | 1.0 |

| Example NB Run # | Total Time of Cat. Prepn. Minutes | % Moly | % N₂ | % H₂O | Acid # | % MOIN | Comments & Observations (Theoretical % Moly) |
|---|---|---|---|---|---|---|---|
| 1 6032-25 | 20 min | 14.0 | 1.10 | 2.27 | 168.17 | 96.5 | Not Filtered B = 90.9% 14.51 |
| 4 5990-31 | 175 min | 13.5 | 1.21 | 2.32 | 164.91 | 96.1 | Not Filtered B = 93.9% 14.05 |
| 2 6032-24 | 23 min | 13.2 | 1.16 | 1.06 | 159.24 | 99.1 | Not Filtered B = 91.2% 13.32 |
| 5 5990-38 | 100 min | 13.2 | 1.07 | 1.54 | 156.81 | 99.9 | Not Filtered B = 92.0% 13.21 |
| 3 6032-26 | 20 min | 11.8 | 1.09 | 2.81 | 140.65 | 96.2 | Not Filtered B = 91.9% 12.27 |
| 6 5990-47 | 118 min | 11.9 | 0.92 | 1.24 | 143.44 | 96.8 | Not Filtered B = 91.7% 12.29 |

Examples 1-3 represent improved, shorter procedure.
Examples 4-6 represent older, established procedure developed by us
(see, for example, U.S. Pat. No. 4,626,596).

We claim:

1. An uncatalyzed method for preparing a catalytically active molybdenum complex which comprises:
   a. mixing essentially undiluted ethylene glycol with essentially undiluted ammonium dimolybdate in a reaction vessel under ambient conditions, such that the ratio of moles of ethylene glycol to gram atoms of molybdenum ranges from about 7:1 to about 20:1 to thereby provide a solution consisting essentially of said undiluted ammonium dimolybdate in said essentially undiluted ethylene glycol,
   b. heating said mixture to a temperature of about 25° C. to about 100° C. while simultaneously reducing the pressure to a pressure of about 5 to about 100 mm of Hg over a period of time ranging from about 5 to about 60 minutes with agitation while removing volatilized reaction by-products, and
   c. thereafter returning said reaction mixture to ambient conditions and recovering an essentially solids free, clear catalytically active solution consisting essentially of a molybdenum/ethylene glycol complex in unreacted ethylene glycol having a molybdenum content of about 10 to about 15 wt. % of molybdenum.

2. A method as in claim 1 wherein:
   the mole ratio of ethylene glycol to gram atoms of molybdenum in the initial reaction mixture is within the range of about 9 to 11,
   the reaction mixture, over a period of time ranging from about 15 to about 40 minutes, is heated to a temperature of about 100° C. while the pressure is simultaneously reduced to about 15 to 60 mm of Hg and
   the reaction mixture is then brought back to ambient conditions of temperature and pressure,
   wherein the evolved reaction products removed overhead constitute about 8 to about 10 wt. % of the charge mixture and
   wherein the final solution contains about 11 to about 14 wt. % of molybdenum.

3. An uncatalyzed method for preparing a catalytically active molybdenum complex which comprises:
   a. preparing a feed mixture by mixing essentially undiluted ethylene glycol with essentially undiluted ammonium dimolybdate in a reaction vessel at a temperature of about 20° about 30° C. and at atmosphereic pressure, such that the ratio of moles of ethylene glycol to gram atoms of molybdenum ranges from about 7:1 to about 20:1 to thereby provide a solution consisting essentially of said undiluted ammonium dimolybdate in said essentially undiluted ethylene glycol,
   b. heating said feed mixture to a temperature of about 25° C. to about 150° C. while simultaneously reducing the pressure to a pressure of about 10 to about 80 mm of Hg over a period of time ranging from about 10 to about 50 minutes with agitation while removing volatilized reaction by-products, and c. holding said mixture at said temperature and subatmospheric pressure conditions established in step b. for a period of time of about 2 to about 30 minutes sufficient to complete the complex formation reaction, as evidenced by the formation of a solids free solution of said complex in said unreacted ethylene glycol, d. thereafter returning said reaction mixture to said initial conditions of temperature and pressure and e. recovering an essentially solids free, clear catalytically active solution consisting essentially of a molybdenum/ethylene glycol complex in unreacted ethylene glycol having a molybdenum content of about 10 to about 15 wt. % of molybdenum, said recovered complex of step e. constituting about 88 to about 95 wt. % of the charge mixture and containing about 1 to about 3 wt. % of water.

4. A method as in claim 3 wherein:

in step a. the ratio of moles of ethylene glycol to gram atoms of molybdenum ranges from about 9 to about 11, in step b. the feed mixture is heated to a temperature of about 25° to about 120° C. over a period of about 10 to about 50 minutes while simultaneously reducing the pressure to about 10 to about 88 mm Hg and in step c. the mixture is held at the temperature and pressure established in step b. for about 4 to about 25 minutes said recovered complex of step e. constituting about 88 to about 95 wt. % of the charge.

5. A method as in claim 3 wherein:

in step a. the ratio of moles of ethylene glycol to gram atoms of molybdenum ranges from about 9 to about 11, in step b. the feed mixture is heated to a temperature of about 25° to about 100° C. over a period of about 10 to about 50 minutes while simultaneously reducing the pressure to about 15 to about 60 mm Hg and in step c. the mixture is held at the temperature and pressure established in step b. for about 6 to about 20 minutes said recovered complex of step e. constituting about 90 to about 92 wt. % of the charge mixture and contains about 11 to about 14 wt. % of molybdenum.

* * * * *